US011478441B2

(12) United States Patent
Bar-Or et al.

(10) Patent No.: US 11,478,441 B2
(45) Date of Patent: Oct. 25, 2022

(54) TREATMENT OF DISEASE WITH N-ACETYL KYNURENINE

(71) Applicant: AMPIO PHARMACEUTICALS, INC., Englewood, CO (US)

(72) Inventors: David Bar-Or, Englewood, CO (US); Leonard T. Rael, Centennial, CO (US); Raphael Bar-Or, Denver, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 218 days.

(21) Appl. No.: 17/023,966

(22) Filed: Sep. 17, 2020

(65) Prior Publication Data

US 2021/0069140 A1    Mar. 11, 2021

Related U.S. Application Data

(62) Division of application No. 16/328,976, filed as application No. PCT/US2017/048662 on Aug. 25, 2017, now abandoned.

(60) Provisional application No. 62/381,824, filed on Aug. 31, 2016.

(51) Int. Cl.
| | |
|---|---|
| *A61K 31/198* | (2006.01) |
| *A61K 45/06* | (2006.01) |
| *A61P 37/06* | (2006.01) |
| *A61P 19/02* | (2006.01) |
| *A61P 29/00* | (2006.01) |
| *A61K 9/00* | (2006.01) |

(52) U.S. Cl.
CPC ............ *A61K 31/198* (2013.01); *A61K 45/06* (2013.01); *A61P 19/02* (2018.01); *A61P 29/00* (2018.01); *A61P 37/06* (2018.01); *A61K 9/0019* (2013.01)

(58) Field of Classification Search
None
See application file for complete search history.

(56) References Cited

U.S. PATENT DOCUMENTS

| | | | |
|---|---|---|---|
| 2014/0234409 | A1 | 8/2014 | Meijerink et al. |
| 2015/0343037 | A1 | 12/2015 | Duque et al. |
| 2016/0032334 | A1 | 2/2016 | Abele et al. |
| 2019/0201360 | A1 | 7/2019 | Bar-Or et al. |

FOREIGN PATENT DOCUMENTS

| | | |
|---|---|---|
| WO | WO 2009/040849 | 4/2009 |
| WO | WO 2010/041288 | 4/2010 |
| WO | WO 2016/044922 | 3/2016 |
| WO | WO 2016/079708 | 5/2016 |

OTHER PUBLICATIONS

Ocampo et al. Oxidative Medicine and Cellular Longevity vol. 2014, Article ID 646909, 22 pages (Year: 2014).*
Bar-Or et al., "A Randomized Clinical Trial to Evaluate Two Doses of an Intra-Articular Injection of LMWF-5A in Adults with Pain Due to Osteoarthritis of the Knee," PloS One, 2014, vol. 9, e87910.
Bellocchi et al., "Quantum mechanics/molecular mechanics (QM/MM) modeling of the irreversible transamination of l-kynurenine to kynurenic acid: The round dance of kynurenine aminotransferase II," Biochimica et Biophysica Acta (BBA)—Proteins and Proteomics, 2009, vol. 1794, Iss. 12, pp. 1802-1812.
Boasso et al., HIV inhibits CD4+ T-cell proliferation by inducing indoleamine 2,3-dioxygenase in plasmacytoid dendritic cells Blood, 2007, vol. 109, Iss. 8, pp. 3351-3359.
Chiarugi et al., "Tryptophan availability selectively limits NO-synthase induction in macrophages," Journal of Leukocyte Biology, 2003, vol. 73, Iss. 1, pp. 172-177.
Cuq et al., "Tryptophan degradation during heat treatments: Part 1—The degradation of free tryptophan," Food Chemistry, 1983, vol. 12, Iss. 1, pp. 1-14.
Darcy et al. "An Observational Cohort Study of the Kynurenine to Tryptophan Ratio in Sepsis: Association with Impaired Immune and Microvascular Function," PLoS One, 2011, vol. 6, Iss. 6, e21185, 8 pages.
Djouad et al., "Transcriptional profiles discriminate bone marrow-derived and synovium-derived mesenchymal stem cells," Arthritis Research & Therapy, 2005, vol. 7, Iss. 6, pp. R1304-R1315.
Fallarino et al., "T cell apoptosis by tryptophan catabolism," Cell Death and Differentiation, 2002, vol. 9, Iss. 10, pp. 1069-1077.
Fallarino et al., "The Combined Effects of Tryptophan Starvation and Tryptophan Catabolites Down-Regulate T Cell Receptor ζ-Chain and Induce a Regulatory Phenotype in Naive T Cells," The Journal of Immunology, 2006, vol. 176, Iss. 11, pp. 6752-6761.
Grunnet et al., "Cytokines and Type 1 Diabetes: A Numbers Game," Diabetes, 2011, vol. 60, Iss. 3, pp. 697-699.
Hains et al., "UV filters in the lens of the thirteen lined ground squirrel (*Spermophilus tridecemlineatus*)," Experimental Eye Research, 2006, vol. 82, Iss. 4, pp. 730-737.
Harden et al., "The tryptophan metabolism enzyme L-kynureninase is a novel inflammatory factor in psoriasis and other inflammatory diseases," Journal of Allergy and Clinical Immunology, 2016, vol. 137, Iss. 6, pp. 1830-1840.
Igarashi et al., "Photoreactivity of Amino Acids: Tryptophan-induced Photochemical Events via Reactive Oxygen Species Generation," Analytical Sciences, 2007, vol. 23, No. 8, pp. 943-948.
Kennard et al., "Crystal Structure of N-Acetylkynurenine," Australian Journal of Chemistry, 1979, vol. 32, Iss. 4, pp. 911-915. (Abstract only).
Keszthelyi et al., "Understanding the role of tryptophan and serotonin metabolism in gastrointestinal function," Neurogastroenterology & Motility, 2009, vol. 21, Iss. 12, pp. 1239-1249.

(Continued)

*Primary Examiner* — Jeffrey S Lundgren
*Assistant Examiner* — Michael J Schmitt
(74) *Attorney, Agent, or Firm* — Sheridan Ross P.C.

(57) ABSTRACT

The invention provides a method, composition and kit for treating T-cell mediated diseases, degenerative joint diseases or diseases mediated by platelet activating factor (PAF) comprising administering to an animal in need thereof, an effective amount a pharmaceutical composition containing N-acetyl-kynurenine (NAK) or pharmaceutically acceptable salts thereof as the active ingredient.

20 Claims, 4 Drawing Sheets

(56) References Cited

OTHER PUBLICATIONS

Kimura et al., "Aryl hydrocarbon receptor in combination with Stat1 regulates LPS-induced inflammatory responses," Journal of Experimental Medicine, 2009, vol. 206, Iss. 9, pp. 2027-2035.

Krause et al., "The Tryptophan Metabolite 3-Hydroxyanthranilic Acid Plays Anti-Inflammatory and Neuroprotective Roles During Inflammation," The American Journal of Pathology, 2011, vol. 179, Iss. 3, pp. 1360-1372.

Meyer et al., "Suitability of Recombinant *Escherichia coli* and *Pseudomonas putida* Strains for Selective Biotransformation of m-Nitrotoluene by Xylene Monooxygenase," Applied and Environmental Microbiology, 2005, vol. 71, Iss. 11, pp. 6624-6632.

Mezrich et al. "An Interaction between Kynurenine and the Aryl Hydrocarbon Receptor Can Generate Regulatory T Cells," The Journal of Immunology, 2010, vol. 185, Iss. 6, pp. 3190-3198.

Michalowska et al., "New insights into tryptophan and its metabolites in the regulation of bone metabolism," Journal of Physiology and Pharmacology, 2015, vol. 66, No. 6, Article 2, 18 pages.

Moffett et al., "Tryptophan and the immune response," Immunology and Cell Biology, 2003, vol. 81, Iss. 4, pp. 247-265.

Moroni et al., "Kynurenic acid actions in brain and periphery," International Congress Series, 2007, vol. 1304, pp. 305-313.

Moroni et al., "Kynurenic acid: a metabolite with multiple actions and multiple targets in brain and periphery," Journal of Neural Transmission, 2012, vol. 119, Iss. 2, pp. 133-139.

Munn et al., "Inhibition of T Cell Proliferation by Macrophage Tryptophan Catabolism," Journal of Experimental Medicine, 1999, vol. 189, Iss. 9, pp. 1363-1372.

Nakahama et al., "Aryl hydrocarbon receptor deficiency in T cells suppresses the development of collagen-induced arthritis," Proceedings of the National Academy of Sciences of the United States of America, 2011, vol. 108, Iss. 34, pp. 14222-14227.

Nguyen et al., "Aryl hydrocarbon receptor and kynurenine: recent advances in autoimmune disease research," Frontiers in Immunology, 2014, vol. 5, Article 551, 6 pages.

Nguyen et al., "Aryl hydrocarbon receptor negatively regulates dendritic cell immunogenicity via a kynurenine-dependent mechanism," Proceedings of the National Academy of Sciences of the United States of America, 2010, vol. 107, Iss. 46, pp. 19961-19966.

Ocampo et al., "Kynurenines with Neuroactive and Redox Properties: Relevance to Aging and Brain Diseases," Oxidative Medicine and Cellular Longevity, 2014, vol. 2014, Article ID 646909, 22 pages.

Sekkaï et al., "Inhibition of Nitric Oxide Synthase Expression and Activity in Macrophages by 3-Hydroxyanthranilic Acid, a Tryptophan Metabolite," Archives of Biochemistry and Biophysics, 1997, vol. 340, Iss. 1, pp. 117-123.

Stevens et al., "The aryl hydrocarbon receptor: a perspective on potential roles in the immune system," Immunology, 2009, vol. 127, Iss. 3, pp. 299-311.

Stone et al., "Kynurenine pathway inhibition as a therapeutic strategy for neuroprotection," The FEBS Journal, 2012, vol. 279, Iss. 8, pp. 1386-1397.

Szántó et al., "Inhibition of indoleamine 2,3-dioxygenase-mediated tryptophan catabolism accelerates collagen-induced arthritis in mice," Arthritis Research & Therapy, 2007, vol. 9, R50, 7 pages.

Vogel et al., "Cross-talk between Aryl Hydrocarbon Receptor and the Inflammatory Response: Role for Nuclear Factor-κB," The Journal of Biological Chemistry, 2014, vol. 289, Iss. 3, pp. 1866-1875.

International Search Report and Written Opinion for International (PCT) Patent Application No. PCT/US17/48662 dated Nov. 7, 2017, 9 pages.

International Preliminary Report on Patentability for International (PCT) Patent Application No. PCT/US17/48662 dated Mar. 14, 2019, 8 pages.

Official Action for U.S. Appl. No. 16/328,976 dated Jul. 2, 2019, 7 pages.

Official Action for U.S. Appl. No. 16/328,976 dated Sep. 30, 2019, 7 pages.

Official Action for U.S. Appl. No. 16/328,976 dated Jan. 17, 2020, 9 pages.

\* cited by examiner

TREATMENT OF DISEASE WITH N-ACETYL KYNURENINE

CROSS-REFERENCE TO RELATED APPLICATIONS

This application is a divisional of U.S. patent application Ser. No. 16/328,976, filed Feb. 27, 2019; which is a national stage application under 35 U.S.C. 371 of PCT Application No. PCT/US2017/048662 having an international filing date of Aug. 25, 2017, which designated the United States; which PCT application claims the benefit of priority under 35 U.S.C. § 119(e) to U.S. Provisional Patent Application No. 62/381,824, filed Aug. 31, 2016. The entire disclosures of U.S. patent application Ser. No. 16/328,976, PCT Application No. PCT/US2017/048662 and U.S. Provisional Patent Application No. 62/381,824 are incorporated herein by reference in their entirety.

FIELD OF THE INVENTION

The invention relates to a method, composition and kit for treating T-cell mediated diseases, degenerative joint diseases or diseases mediated by platelet activating factor (PAF) by administration of a pharmaceutical composition containing N-acetyl-kynurenine (NAK) as the active ingredient and related pharmaceutical compositions.

BACKGROUND

The low molecular weight fraction of 5% human serum albumin (LMWFSA) is a biological that has anti-inflammatory and pain relief properties in the treatment of various chronic conditions such as osteoarthritis. In addition to marked improvements in clinical trials, LMWFSA increases biomarkers of resolution of inflammation with compensatory decreases in pro-inflammatory mediators. Individually, various known components of LMWFSA have some anti-inflammatory activity in various in vitro tests although these activity levels are less than the combined effect of LMWFSA. The cyclic compound derived from the N-terminus of human serum albumin (HSA), aspartate-alanine diketopiperazine (DA-DKP), is found in LMWFSA in micromolar concentrations that are high enough to decrease pro-inflammatory cytokine release from PBMC and T-cell lines following stimulation. N-acetyl tryptophan (NAT) is present at millimolar concentrations in LMWFSA since it is added to the parent 5% HSA solution and acts as an anti-oxidant to provide protection to the HSA protein in the heating phase of manufacturing albumin. NAT is known to have immuno-modulatory properties via inhibition of neurokinin 1 receptor (NK1R) thereby regulating important pro-inflammatory signals in immune cells. LMWFSA is a highly complex mixture containing many individual components, the vast majority of which are of previously unknown function.

N-acetyl-kynurenine (NAK) has been reported in the literature (Kennard, et al., "Crystal structure of N-acetylkynurenine. Aust. J Chem 2979; 32:911-915; Hains et al., "UV filters in the lens of the thirteen lined ground squirrel (*Spermophilus tridecemlineatus*). Exp Ey Res. 2006 April; 82(4):730-737; Stone et al., "Kynurenine pathway inhibition as a Therapeutic Strategy for Neuroprotection. FEBS Journal 279 (2012) 1386-1397; Michalowska, et al., "New Insights into Tryptophan and is Metabolites in the Regulation of Bone Metabolism. JPP No 6; 2015, article 2). However, no biological activity of N-acetyl-kynurenine has been reported, with the exception as a UV filter in the lenses of the ground squirrel (Hains et al.). Further, the presence of this compound in low molecular weight fractions of human serum albumin has not been previously recognized.

SUMMARY OF THE INVENTION

One embodiment of the invention relates to a method of treating a T-cell mediated disease, a degenerative joint disease, or a disease mediated by platelet-activating factor (PAF), comprising administering to an animal in need thereof, an effective amount of a pharmaceutical composition consisting essentially of N-acetyl-kynurenine or a pharmaceutically acceptable salt thereof.

Another embodiment of the invention relates to a method of treating a T-cell mediated disease, a degenerative joint disease, or a disease mediated by platelet activating factor, comprising administering to an animal in need thereof, an effective amount of a pharmaceutical composition comprising N-acetyl-kynurenine or a pharmaceutically acceptable salt thereof and a second active agent effective to treat the disease. In one aspect, the second active agent effective to treat the disease can be selected from an analgesic, an anti-inflammatory drug, and combinations thereof.

Another embodiment of the invention relates to a method of treating a T-cell mediated disease, a degenerative joint disease, or a disease mediated by platelet activating factor comprising administering to an animal in need thereof an effective amount of a pharmaceutical composition comprising N-acetyl-kynurenine or a pharmaceutically acceptable salt thereof in a concentration greater than about 50 µM, about 60 µM, about 70 µM, about 80 µM, about 90 µM or about 100 µM.

In one aspect of any one of the embodiments of the invention, the T-cell mediated disease can be selected from graft rejection, graft versus host disease, an unwanted delayed-type hypersensitivity reaction, a T-cell mediated pulmonary disease or an autoimmune disease.

In yet another aspect of any one of the embodiments of the invention, the T-cell mediated disease is multiple sclerosis, inclusion body myositis (IBM), amyotrophic lateral sclerosis (ALS), neuritis, polymyositis, psoriasis, vitiligo, Sjogren's syndrome, rheumatoid arthritis, Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia, or systemic lupus erythematosus.

In still another aspect of any one of the embodiments of the invention, the T-cell mediated disease is an inflammatory disease.

In still another aspect of any one of the embodiments of the invention, the degenerative joint disease is osteoarthritis. In one aspect, the osteoarthritis is of the knee, hip, shoulder, hand or spine.

In yet another aspect of any one of the embodiments of the invention, the disease mediated by platelet activating factor can be selected from an allergy, acute respiratory distress syndrome, asthma, bronchitis, emphysema, a respiratory infection, sepsis and shock In another aspect of any one of the embodiments of the invention, the pharmaceutical composition is administered by an administration route selected from injection, topical, local, transdermal, inhalation and eye drops. In one aspect, the pharmaceutical composition is administered by intra-articular injection.

Another embodiment of the invention relates to N-acetyl-kynurenine and pharmaceutically acceptable salts thereof for use in the treatment of a disease selected from the group consisting of a T-cell mediated disease, a degenerative joint disease, and a disease mediated by platelet activating factor.

Another embodiment of the invention relates to a pharmaceutical composition comprising an active pharmaceutical ingredient consisting essentially of N-acetyl-kynurenine or a pharmaceutically acceptable salt, and a pharmaceutically-acceptable carrier.

Another embodiment of the invention relates to a pharmaceutical composition that comprises N-acetyl-kynurenine or a pharmaceutically acceptable salt thereof and a second active agent effective to treat a disease selected from a T-cell mediated disease, a degenerative joint disease, and a disease mediated by platelet activating factor. In one aspect, the second active agent can be selected from an analgesic, an anti-inflammatory drug and combinations thereof.

Another embodiment of the invention relates to a pharmaceutical composition, comprising N-acetyl-kynurenine or a pharmaceutically acceptable salt thereof in a concentration greater than about 50 µM.

Another embodiment of the invention relates to a kit comprising a composition comprising an active pharmaceutical ingredient consisting essentially of N-acetyl-kynurenine or a pharmaceutically acceptable salt, and a pharmaceutically-acceptable carrier, wherein the composition is in a container.

DETAILED DESCRIPTION OF THE INVENTION

Figure 1:
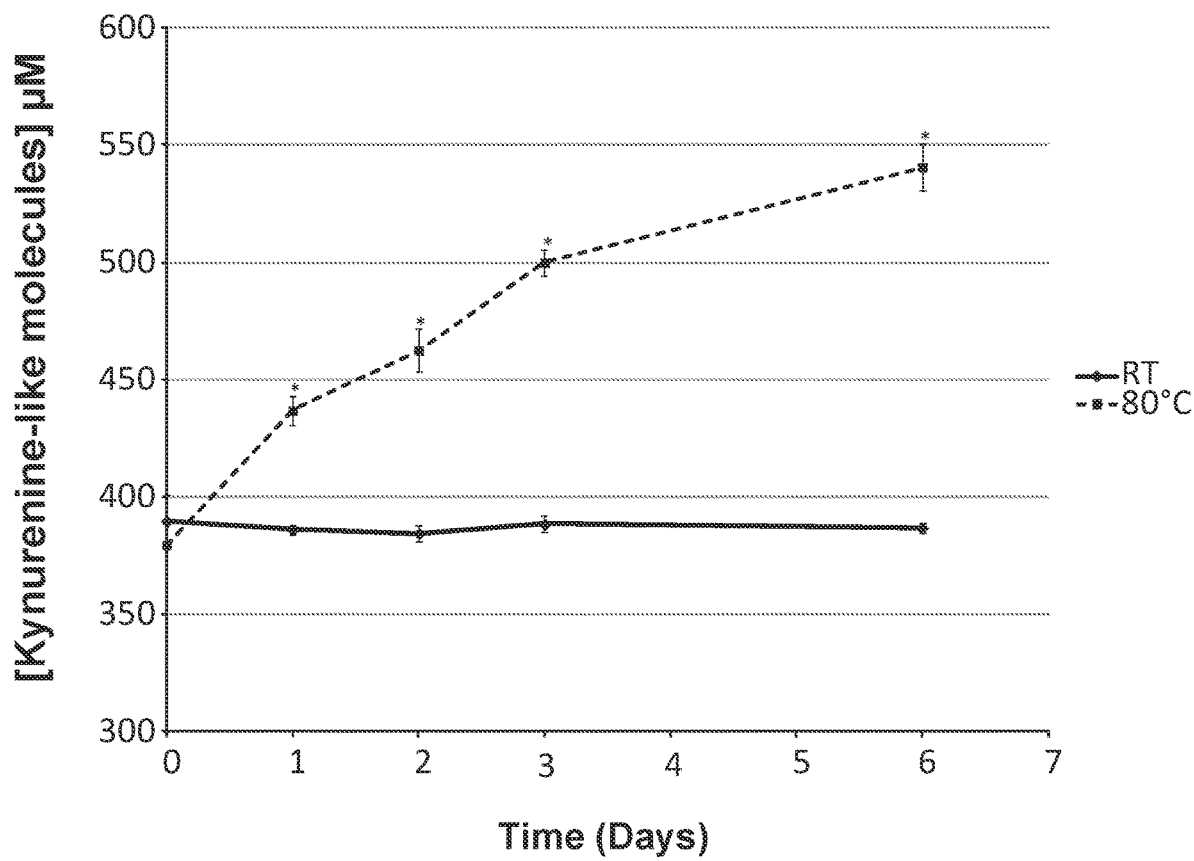
FIG. 1: Colorimetric detection (492 nm) of kynurenine-like molecules in LMWFSA using Ehrlich's assay. Vials of LMWFSA were incubated at room temperature (RT, solid line) or 80° C. (dotted line) for 6 days. Data is presented as concentration (µM) of kynurenine-like molecules±SD after repeating the experiment on 3 different occasions with statistical significance (p<0.05) indicated with an asterisk (*).

The present invention provides a method of treating a T-cell mediated disease, a degenerative joint disease, or a disease mediated by platelet activating factor. The method comprises administering an effective amount of a pharmaceutical composition comprising N-acetyl-kynurenine (NAK) to an animal having a need thereof. The invention also provides for a pharmaceutical composition and kit comprising NAK for the treatment of a T-cell mediated disease, a degenerative joint disease, or a disease mediated by platelet activating factor.

The inventors have demonstrated that NAT is non-enzymatically degraded during long-term storage of LMWFSA with high heat accelerating degradation, and more importantly, that N-acetyl kynurenine (NAK) is a major degradation product found in LMWFSA with other minor NAT degradation products being present. The presence of kynurenine-like molecules in LMWFSA is important to the overall anti-inflammatory effect of LMWFSA. Without being bound by theory, this effect is believed to be mediated via various immune cell receptors such as binding to the aryl hydrocarbon receptor (AHR) by kynurenines resulting in an increase in anti-inflammatory mediators. Therefore, N-acetyl kynurenine and other NAT breakdown products are now recognized to have anti-inflammatory and pain relief properties.

NAK has now been found to be present in low molecular weight fractions (LMWF) of human serum albumin. One such LMWF is LMWFSA, a biologic derived from the less than 5 kDa fraction of human serum albumin. In clinical trials, a single intra-articular injection of LMWFSA resulted in a significant 42.3% reduction in pain observed 4 weeks following injection that persisted to the completion of the trial versus saline controls (Bar-Or D, et al. A randomized clinical trial to evaluate two doses of an intra-articular injection of LMWF-5A in adults with pain due to osteoarthritis of the knee. *PloS one* 2014; 9:e87910).

Methods of making low molecular weight fractions of human serum albumin are known. For example, using an ultrafiltration separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDA, less than about 40 kDa, less than 30 kDa, less than about 20 kDa, less than about 10 kDa, less than about 5 kDa, less than about 3 kDa. Preferably, the filtrate comprises components having molecular weights less than about 5 Da (also referred to as "<5000 MW" or LMWF5A). This <5000 MW or LMWF5A fraction or filtrate contains DA-DKP which is formed after the dipeptide aspartate-alanine is cleaved from albumin and subsequently cyclized into the diketopiperazine. The inventors have now determined, as discussed in the Example section below, that NAK is also present in this fraction or filtrate.

Additional methods of making or synthesizing NAK include synthesizing NAK by standard methods from a starting solution of N-acetyl tryptophan and/or synthesizing NAK by standard methods from a starting solution of kynurenine in the presence of N-acetyl tranferase. The kynurenine pathway is disclosed in Stone et al. as well as in Michalowska, et al.

Pharmaceutically acceptable salts of NAK of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

T-cell mediated diseases represent a large number of immune system disorders. In particular, T-cells are thought to be the cells that start and perpetuate autoimmune diseases. Autoimmune diseases are a group of eighty serious, chronic illnesses that afflict millions of people in the United States alone. Autoimmune diseases are characterized by reactivity of the immune system to endogenous (self) antigens. These immune responses to self antigens are maintained by the persistent or recurrent activation of self-reactive T-cells and, directly or indirectly, the self-reactive T-cells are responsible for the characteristic tissue injury and destruction seen in autoimmune diseases. Although many treatments for autoimmune diseases and other T-cell mediated diseases have been proposed, there is still a need for additional treatments.

T-cell mediated diseases include graft rejection, graft versus host disease, unwanted delayed-type hypersensitivity reactions (such as delayed-type allergic reactions), T-cell mediated pulmonary diseases, and autoimmune diseases. T-cell mediated pulmonary diseases include sarcoidosis, hypersensitivity pneumonitis, acute interstitial pneumonitis, alveolitis, pulmonary fibrosis, idiopathic pulmonary fibrosis and other diseases characterized by inflammatory lung damage. Autoimmune diseases include multiple sclerosis, inclusion body myositis (IBM), amyotrophic lateral sclerosis (ALS), neuritis, polymyositis, psoriasis, vitiligo, Sjogren's syndrome, rheumatoid arthritis, Type 1 diabetes, autoimmune pancreatitis, inflammatory bowel diseases (e.g., Crohn's disease and ulcerative colitis), celiac disease, glomerulonephritis, scleroderma, sarcoidosis, autoimmune thyroid diseases (e.g., Hashimoto's thyroiditis and Graves disease), myasthenia gravis, Addison's disease, autoimmune uveoretinitis, pemphigus vulgaris, primary biliary cirrhosis, pernicious anemia, and systemic lupus erythematosis.

PAF has been reported to play a role in a variety of diseases and conditions. These diseases and conditions include acute respiratory distress syndrome, allergies, arthritis, asthma, autoimmune diseases, bronchitis, cardiovascular disease, Crohn's disease, cystic fibrosis, emphysema, gastrointestinal ulceration, inflammation, inflammatory bowel disease, ischemia, multiple organ dysfunction syndrome, myocardial infarction, neoplastic diseases, ophthalmic inflammation, pain, psoriasis, respiratory infections, sepsis, shock, and ulcerative colitis. PAF also mediates platelet aggregation.

A degenerative joint disease is a gradual deterioration of the articular cartilage that covers joints. A degenerative joint disease (osteoarthritis) is a noninfectious progressive disorder of the weightbearing joints. The normal articular joint cartilage is smooth, white, and translucent. It is composed of cartilage cells (chondrocytes) imbedded in a sponge-like matrix made of collagen, protein polysaccharides, and water. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density while any remaining cartilage begins to fray. Eventually, osteophytes (spurs of new bone) covered by cartilage form at the edge of the joint. As mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint disease is the result of mechanical instabilities or aging changes within the joint. This includes old age degenerative arthritis and, in younger individuals, may be the result of injuries, bruises, abnormal joint configuration (i.e. hip dysplasia), or mechanical wear from anterior cruciate ligament rupture, patellar luxation, or osteochondritis dissecans, for example. Degenerative joint disease can occur at any joint in the body, including without limitation, knee, hip, shoulder, hand and spine.

Conventional pharmaceutical therapies for degenerative joint disease include acetaminophen, nonsteroidal anti-inflammatory drugs (NSAIDS), narcotics, and corticosteroids.

The pharmaceutical composition of the invention comprising NAK or pharmaceutically acceptable salts thereof is administered to an animal in need of treatment. Preferably, the animal is a mammal, such as a rabbit, goat, dog, cat, horse or human. Effective dosage amounts may vary with the severity of the disease or condition, the route(s) of administration, the duration of the treatment, the identity of any other drugs being administered to the animal, the age, size and species of the animal, and like factors known in the medical and veterinary arts.

NAK as used in the present invention is used as an active ingredient. "Active ingredient" is used herein to mean a compound having therapeutic, pharmaceutical or pharmacological activity, and particularly, the therapeutic, pharmaceutical or pharmacological activity described herein. NAK is not used in the present invention as a carrier or as part of a carrier system of a pharmaceutical composition. In various embodiments of the invention, the pharmaceutical composition including NAK and pharmaceutically acceptable salts thereof can be characterized as having an absence of or being free of DA-DKP and/or other components of a LMWF of human serum albumin. Alternatively, the pharmaceutical composition including NAK and pharmaceutically acceptable salts thereof can be characterized as consisting essentially of NAK and pharmaceutically acceptable salts thereof, whereby the composition is open to the inclusion of other elements that do not materially affect the basic and novel characteristics of the composition, which will be appreciated as having an active pharmacological effect in the treatment of a T-cell mediated disease, a degenerative joint disease, and/or a disease mediated by platelet activating factor.

Effective dosage forms, modes of administration and dosage amounts for the compounds of the invention may be determined empirically using the guidance provided herein. It is understood by those skilled in the art that the dosage amount will vary with the particular disease or condition to be treated, the severity of the disease or condition, the route(s) of administration, the duration of the treatment, the identity of any other drugs being administered to the animal, the age, size and species of the animal, and like factors known in the medical and veterinary arts. In general, a suitable dose of a compound of the present invention will be that amount of the compound which is the lowest dose effective to produce a therapeutic effect. However, the dosage will be determined by an attending physician or veterinarian within the scope of sound medical judgment. If desired, an effective daily dose may be administered as two, three, four, five, six or more sub-doses, administered separately at appropriate intervals throughout the day. Administration of the compound should be continued until an acceptable response is achieved.

In particular, an effective dosage amount of NAK or pharmaceutically acceptable salts can be from 10 ng/kg/day to 225 mg/kg/day, preferably from 500 ng/kg/day to 150 mg/kg/day, most preferably from 1 mg/kg/day to 30 mg/kg/day. When given orally to an adult human, the dose will preferably be from about 1 mg/day to about 10 g/day, more preferably the dose will be from about 60 mg/day to about 6 g/day, most preferably the dose will be from about 100 mg/day to about 1200 mg/day, preferably given in several doses. Alternatively, pharmaceutical compositions of the present invention can be administered as a solution, such as by local injection in joints. In such compositions, the NAK or pharmaceutically acceptable salts thereof can be present in concentrations from about 1 µM to about 200 µM, about 5 µM to about 175 µM, about 10 µM to about 150 µM, about 15 µM to about 125 µM, about 20 µM to about 100 µM, about 25 µM to about 75 µM, about 30 µM to about 70 µM, about 35 µM to about 65 µM, or about 40 µM to about 60 µM. In other embodiments, the amount of NAK or pharmaceutically acceptable salts thereof in compositions of the invention can range from any whole number µM concentration to any other whole number µM concentration within the range of from about 1 µM concentration to about 200 µM. In other embodiments, pharmaceutical compositions of the present invention can include NAK or pharmaceutically acceptable salts thereof at concentrations of greater than about 50 µM, greater than about 55 µM, greater than about 60 µM, greater than about 65 µM, greater than about 70 µM, greater than about 75 µM, greater than about 80 µM, greater than about 85 µM, greater than about 90 µM, greater than about 95 µM, greater than about 100 µM, greater than about 110 µM, greater than about 120 µM, greater than about 130 µM, greater than about 140 µM, greater than about 150 µM, greater than about 160 µM, greater than about 170 µM, greater than about 180 µM, greater than about 190 µM, greater than about 200 µM.

The compounds of the present invention may be administered to an animal patient for therapy by any suitable route of administration, including orally, nasally, parenterally (e.g., intravenously, intraperitoneally, subcutaneously, intramuscularly or intraarticularly), transdermally, intraocularly, topically (including buccally and sublingually), and by inhalation and drops (such as eye or nose drops).

While it is possible for a compound of the present invention to be administered alone, it is preferable to administer the compound as a pharmaceutical formulation (composition). The pharmaceutical compositions of the invention comprise NAK or pharmaceutically acceptable salts thereof as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., Remington's Pharmaceutical Sciences.

One embodiment of the invention is a pharmaceutical composition comprising (i) an active pharmaceutical ingredient consisting essentially of N-acetyl-kynurenine or a pharmaceutically acceptable salt thereof, and (ii) a pharmaceutically-acceptable carrier. In such a pharmaceutical composition, reference to an active pharmaceutical ingredient consisting essentially of N-acetyl-kynurenine or a pharmaceutically acceptable salt thereof being in a composition that is otherwise open to the presence of other components means that the composition does not have any active pharmaceutical ingredient other than N-acetyl-kynurenine or a pharmaceutically acceptable salt thereof. Such a composition, however, can include, in addition to the pharmaceutically-acceptable carrier, other non-pharmaceutically active components.

A further embodiment of the invention includes a pharmaceutical composition that comprises N-acetyl-kynurenine or a pharmaceutically acceptable salt thereof and a second active agent. The N-acetyl-kynurenine or a pharmaceutically acceptable salt thereof and the second active agent are present in an amount that is effective to treat a disease selected from a T-cell mediated disease, a degenerative joint disease, and a disease mediated by platelet activating factor. For example, the second active agent can be selected from an analgesic, an anti-inflammatory drug and combinations thereof.

A still further embodiment of the invention includes a pharmaceutical composition that comprises N-acetyl-kynurenine or a pharmaceutically acceptable salt thereof in a concentration greater than about 50 µM. In alternative embodiments, the N-acetyl-kynurenine or a pharmaceutically acceptable salt thereof is present in a concentration greater than about 60 about 70 about 80 about 90 µM or about 100 µM.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., NAK, a prodrug of NAK, a pharmaceutically-acceptable salt of either one of them, or combinations of the foregoing) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for topical administration or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. Drops can be in the form of eye drops.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. A drug-impregnated solid carrier (e.g., a dressing) can also be used for topical administration.

Pharmaceutical formulations include those suitable for administration by inhalation or insufflation or for nasal administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents. Also, drug-coated stents may be used.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

NAK or pharmaceutically acceptable salts thereof may be given in combination with each other and/or in combination with one or more other treatments or drugs suitable for treating the disease or condition. For instance, NAK can be administered prior to, in conjunction with (including simultaneously with), or after the other treatment or drug. In the case of another drug, the drug and NAK, may be administered in separate pharmaceutical compositions or as part of the same pharmaceutical composition.

In addition, the composition of the present invention may also comprise a second drug such as an analgesic (such as lidocaine or paracetoamol), an anti-inflammatory (such as bethamethasone, non-steroid anti-inflammatory drugs (NSAIDs), acetaminophen, ibuprofen, naproxen), and/or other suitable drugs.

Other embodiments of the invention include kits comprising the pharmaceutical products of the present invention are also provided. The kits can comprise a composition comprising NAK or pharmaceutically acceptable salts thereof formulated for administration by injection. The kits may contain unit-dose or multi-dose sealed containers, for example, ampoules and vials, and may be stored in a lyophilized condition requiring only the addition of the sterile liquid carrier, for example water for injection, immediately prior to use. The kits may also be stored in a condition, wherein the contents are ready for direct use or injection. The kits comprise a container comprising NAK or pharmaceutically acceptable salts thereof. The kits may further comprise one or more additional containers each holding one or more other drugs suitable for use in the methods of the invention. Suitable containers include vials, bottles (including with a bottle with a dropper or a squeeze bottle), blister packs, inhalers, jars, nebulizers, packets (e.g., made of foil, plastic, paper, cellophane or another material), syringes and tubes. The kit will also contain instructions for administration of the composition and, optionally, the one or more other drugs suitable for use in the methods of the invention. The instructions may, for instance, be printed on the packaging holding the container(s), may be printed on a label attached to the kit or the container(s), or may be printed on a separate sheet of paper that is included in or with the kit. The packaging holding the container(s) may be, for instance, a box, or the container(s) may wrapped in, for instance, plastic shrink wrap. The kit may also contain other materials which are known in the art and which may be desirable from a commercial and user standpoint.

As used herein, "a" or "an" means one or more.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein.

As used herein, "inhibiting, "inhibit" and similar terms are used herein to mean to reduce, or delay.

As used herein, "treat," "treating" or "treatment" is used herein to mean to reduce (wholly or partially) the symptoms, duration or severity of a disease or condition.

Additional objects, advantages and novel features of the present invention will become apparent to those skilled in the art by consideration of the following non-limiting examples. The following experimental results are provided for purposes of illustration and are not intended to limit the scope of the invention.

Example

This example characterizes LMWFSA using liquid chromatography tandem-mass spectrometry (LCMS-MS) and other techniques to identify non-enzymatic breakdown products of N-acetyl tryptophan (NAT). Thermal forced degradation conditions were also applied in order to increase the amount of NAT breakdown products to improve detection and identification.

The excipient NAT is added at a concentration of 4 mM to 5% commercial solutions of human serum albumin (HSA) for the purpose of stabilizing the protein during the pasteurization process. It has been postulated that NAT provides a protective effect on the free sulfhydryl group (Cys-34) of HSA thereby diminishing protein oxidation. In the study below, the low molecular weight fraction of 5% HSA (LMWFSA) was shown to contain breakdown products of NAT. This is the first study to specifically describe the presence of N-acetyl kynurenine in a solution derived from commercially available HSA. In summary, breakdown products of NAT were detected in LMWFSA with N-acetyl kynurenine being the dominant species. This degradation of NAT in LMWFSA is via a non-enzymatic process since the conversion is facilitated by long term storage and can be accelerated with high heat.

Materials and Methods

Materials

5% human serum albumin (HSA) from Octapharma (Hoboken, N.J.) was used for the production of LMWFSA. Solvents for LCMS analysis were purchased from Fisher Scientific (Pittsburgh, Pa.). 0.9% (w/v) Sodium Chloride (10 mL Saline injection syringe flush, USP) was obtained from Excelsior Medical (Neptune, N.J., USA). All other reagents were obtained from Sigma (St. Louis, Mo.) unless otherwise stated.

Collection of LMWF5A

LMWFSA was isolated by Ampio Pharmaceuticals, Inc. (Englewood, Colo., USA) using a tangential flow filtration (TFF) process with a 5 kDa molecular weight cut-off (MWCO) polyvinylidene difluoride (PVDF) filter membrane (Sartorius Stedim Biotech GmbH, Germany). In accordance with cGMP guidelines, the isolation process involved the removal of the >5 kDa component (primarily HSA) and the aseptic filling of sterile glass vials with 4.2 mL LMWFSA. Each vial was sealed with a rubber stopper and a proper metal closure. The vials were stored in the dark at ambient temperature.

Colorimetric Detection of Kynurenine-Like Molecules in LMWF5A

The quantitation of kynurenine-like species in LMWFSA was detected using a modified method by Meyer et al. ("Suitability of recombinant *Escherichia coli* and *Pseudomonas putida* strains for selective biotransformation of m-nitrotoluene by xylene monooxygenase", Appl Environ Microbiol 71 (2005) 6624-6632). The method is based on the reaction of p-dimethylamino-benzaldehyde (DMAB or Ehrlich's reagent) with primary aromatic amines to form yellow imines in acidic conditions. Briefly, 1004 LMWFSA or kynurenine standard (0-800 µM in 0.9% saline) was combined in triplicate with 100 µL Ehrlich's reagent in a 96-well plate. The plate was read at 492 nm using a SpectraMax M2 plate reader (Molecular Devices, Sunnyvale, Calif., USA). Since a standard for N-acetyl kynurenine was not readily available, kynurenine was used to quantitate kynurenine-like molecules.

LCMS Analysis of LMWF5A

5 µL of LMWF5A was injected on an Acquity UPLC BEH C18 column (Waters, Milford, Mass., USA) connected to an Acquity H-Class liquid chromatography system (Waters, Milford, Mass., USA) and Xevo G2S tandem mass spectrometer (Waters, Milford, Mass., USA). Starting mobile phase conditions consisted of 99% HPLC-grade water with 0.1% TFA (Solvent A) and 1% acetonitrile with 0.1% TFA (Solvent B) at a flow rate of 0.5 mL/min. The gradient was adjusted to 40% Solvent A and 60% Solvent B during the 25 minute run. A 5 minute equilibration was included to return to starting conditions. MS survey conditions consisted of capillary (2.5 kV), sampling cone (30V), source temperature (110° C.), desolvation temperature (500° C.), cone gas (150 L/hr), desolvation gas (850 L/hr) and collision energy (6V). Accurate mass determination was accomplished using leucine enkephalin.

Tandem mass spectrometry (MS-MS) was performed using the same conditions as the LCMS settings above except the collision energy was set at 15V. Also, only [M+]=251.10 was analyzed since it corresponds to the molecular weight of N-acetyl kynurenine in ESI+ mode. The cleavage pattern of [M+]=251.10 was compared to kynurenine ([M+]=209.09).

Thermal Forced Degradation of LMWF5A

LMWFSA was incubated at ambient temperature or 80° C. for 6 days. Aliquots were collected at 0, 1, 2, 3, or 6 days and analyzed in triplicate for kynurenine-like molecules using the colorimetric assay described in Section 2.3. Also, 4 mM N-acetyl tryptophan in 0.9% saline was incubated at 80° C. for 6 days.

Extraction of N-Acetyl Kynurenine from LMWF5A

LMWFSA was injected multiple times using the LCMS method described in Section 2.4. The peak corresponding to N-acetyl kynurenine ([M+]=251.10) was collected, and all fractions were combined. This solution was lyophilized and then reconstituted in 0.9% saline. Kynurenine-like molecules were quantitated in triplicate in this fraction using the colorimetric assay described above.

Data Analysis

A paired Student t-test was applied to all data sets, with statistical significance accepted at $p<0.05$.

Results

Presence of Kynurenine-Like Molecules in LMWFSA

Using Ehrlich's reagent, kynurenine-like molecules were detected and quantitated in LMWF5A (FIG. 1). LMWF5A contained 380-390 µM of kynurenine-like molecules when using kynurenine (KYN) as a standard. Thermal forced degradation of LMWF5A at 80° C. increased the levels of kynurenine-like molecules to 540 µM during the 6 day incubation, or a 42% increase (FIG. 1). Of note, the known components of LMWFSA (NAT, caprylate, or DA-DKP) did not interfere with the assay up to a concentration of 4 mM (data not shown). Kynurenic acid, a breakdown product of KYN, also did not interfere with the assay (data not shown). Additionally, 4 mM NAT in 0.9% saline heated at 80° C. for 6 days resulted in a concentration of 11.6 µM versus undetectable levels of kynurenine-like molecules at t=0. Finally, LMWFSA vials stored at ambient temperature protected from light contained ~10× higher levels of kynurenine-like molecules after 3 years versus starting conditions.

LCMS Analysis of LMWFSA

LMWFSA was also analysed using LCMS methodology. A peak corresponding to the molecular mass of N-acetyl kynurenine ([M+]=251.10) was identified. This peak was isolated by collecting the fraction corresponding to this mass and tested positive with the Ehrlich's assay. Additionally, heating of LMWFSA at 80° C. for 6 days resulted in a 27% increase in the mass corresponding to [M+]=251.10 based on area-under-the-curve (AUC) analysis.

The mass corresponding to [M+]=251.10 was further subjected to a higher collision energy to obtain structural information on the molecule. An MSMS spectra for [M+]=251.10 is presented in FIG. 2A. To determine if this molecule is structurally related to kynurenine (KYN), KYN was also subjected to the same MS-MS conditions at [M+]=209.09 (FIG. 2B). The two MS-MS spectra show strong similarity in that major fragment peaks are observed at m/z of 192.06, 174.05, 146.06, 120.04, and 94.06. These fragments are presented within the dashed box in FIG. 3. Also, the mass of the parent peak of KYN (m/z 209.09) was observed in both spectra indicating that the acetyl group is cleaved from N-acetyl kynurenine under these MS-MS conditions.

Figure 2A:
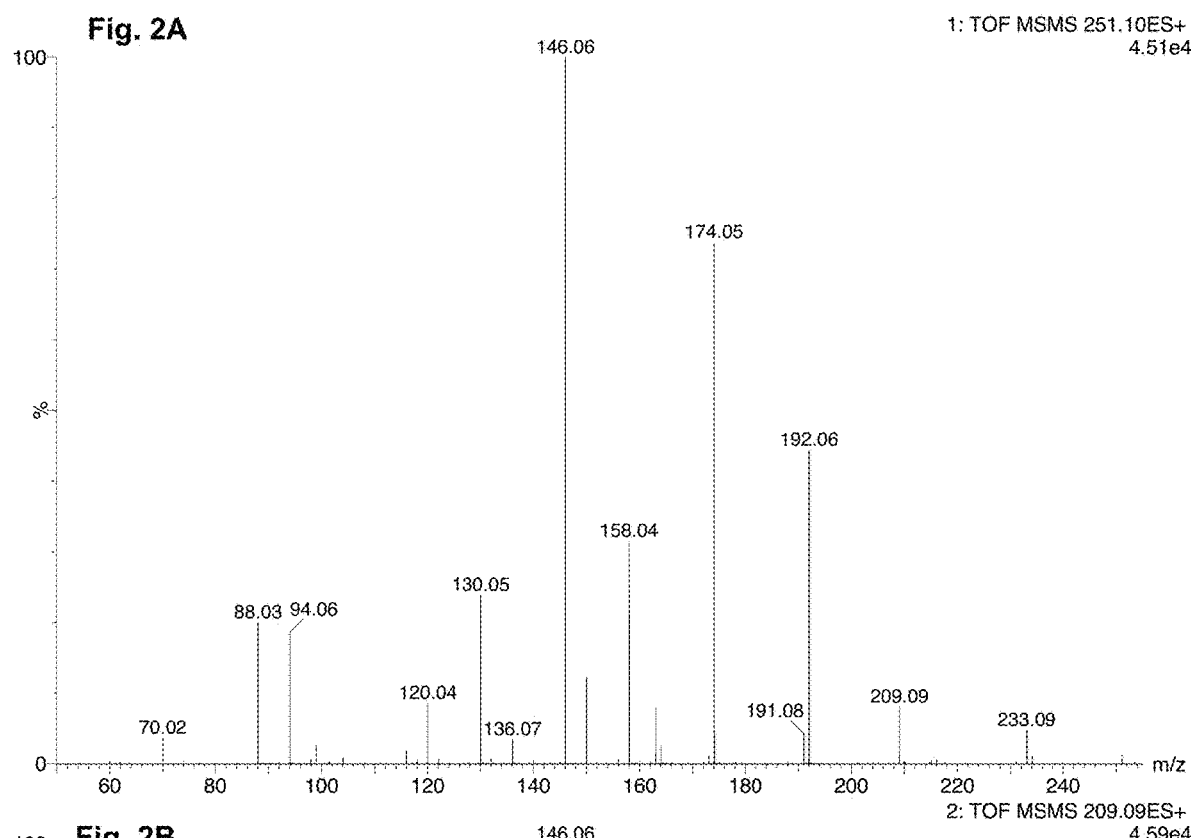
FIG. 2A and FIG. 2B: LCMS-MS spectra of N-acetyl kynurenine ([M+]=251.10) (FIG. 2A) identified in LMWFSA and kynurenine ([M+]=209.09) stock solution in saline (FIG. 2B). Structural similarities in the two spectra include mass fragments at m/z 192.06, 174.05, 146.06, 120.04, and 94.06. Structural differences in the two spectra include mass fragments at m/z 158.04, 130.05, 88.03, and 70.02 seen in the N-acetyl kynurenine spectrum only.
Figure 2B:
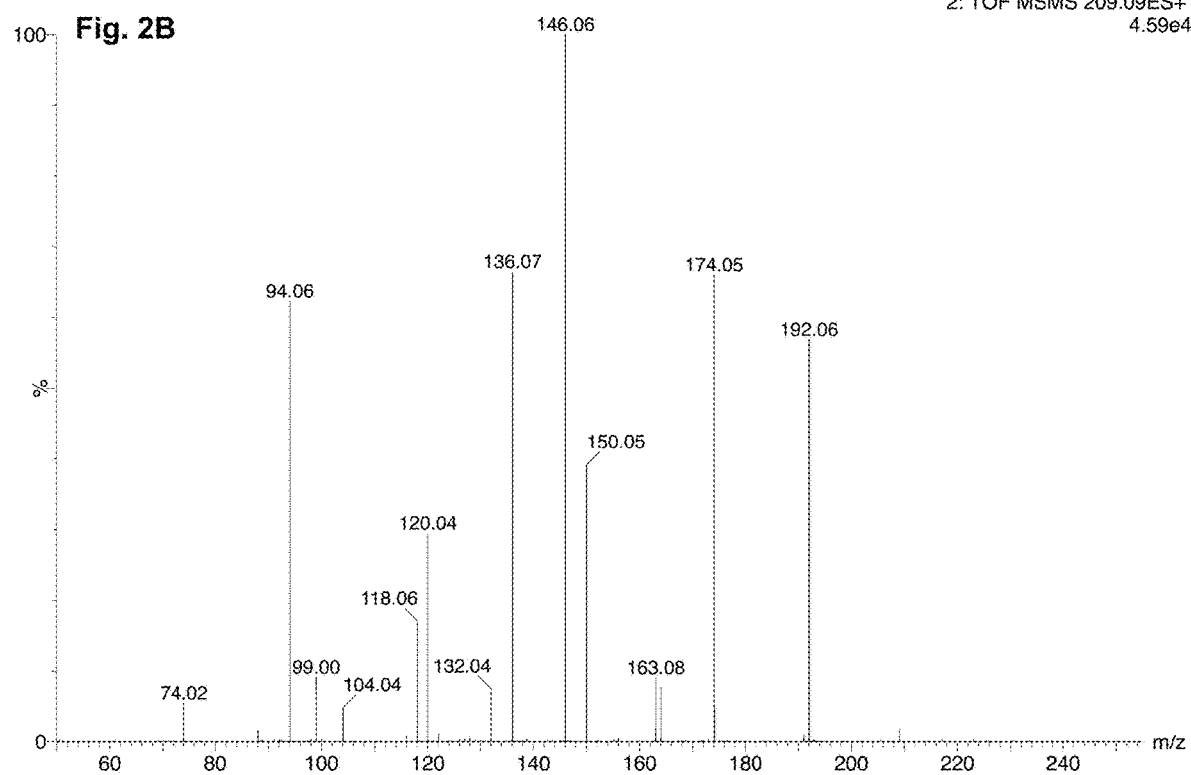
Figure 3:
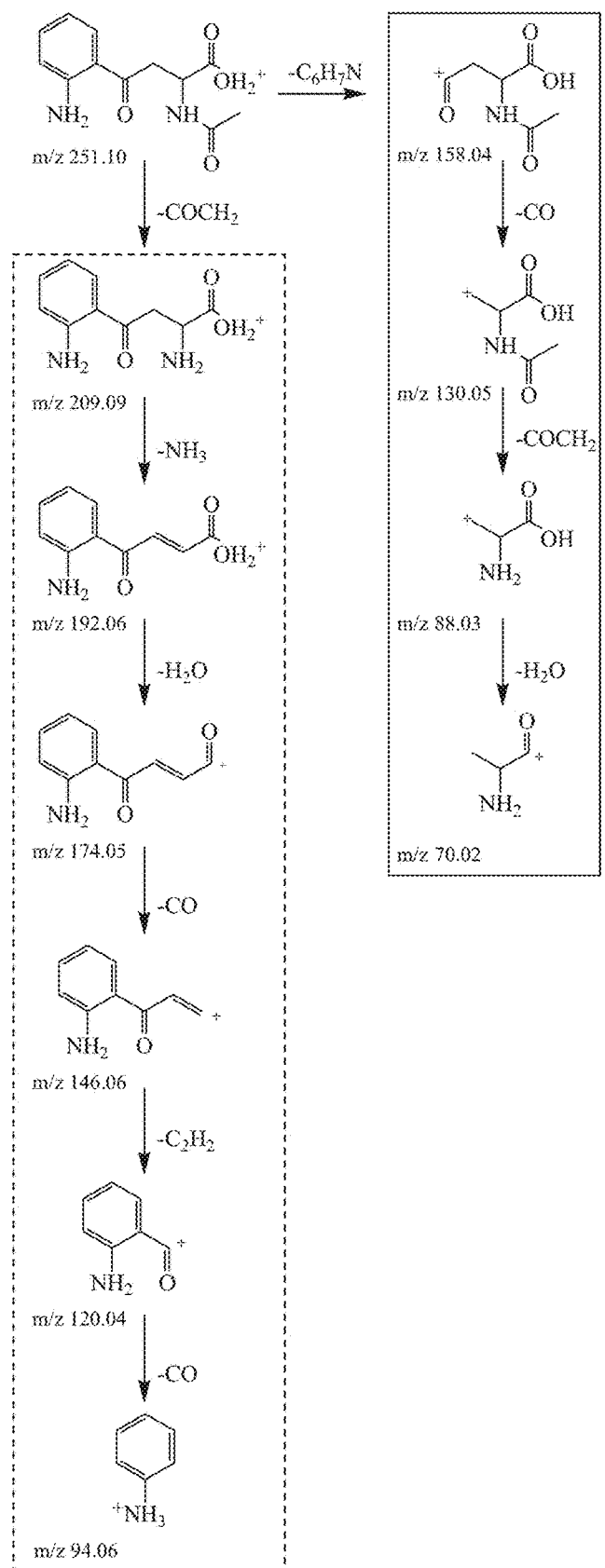
FIG. 3: Proposed fragment structures for the observed product ions using the LCMS-MS conditions listed in the Materials and Methods section. The structural similarities of N-acetyl kynurenine ([M+]=251.10) and kynurenine ([M+]=209.09) include mass fragments at m/z 192.06, 174.05, 146.06, 120.04, and 94.06 (dotted box). The structural differences of N-acetyl kynurenine and kynurenine include mass fragments at m/z 158.04, 130.05, 88.03, and 70.02 (solid box).

Significant differences between the two MS-MS spectra at m/z of 158.04, 130.05, 88.03, and 70.02 were observed for N-acetyl kynurenine (FIG. 2A). For the mass fragments at m/z of 158.04 and 130.05, these correspond to fragments that still contain the N-acetyl group thereby strongly suggesting that the parent compound is N-acetyl kynurenine (FIG. 3—solid box). The mass fragment at m/z of 88.03 is also present in the KYN MS-MS spectra at much lower intensity. This fragment does not contain the N-acetyl group, but it is more intense in the N-acetyl kynurenine MS-MS spectra likely due to the specific MS conditions. The same argument can be made for the mass fragment at m/z 70.02.

Additional Breakdown Products of NAT in LMWF5A

Figure 4:
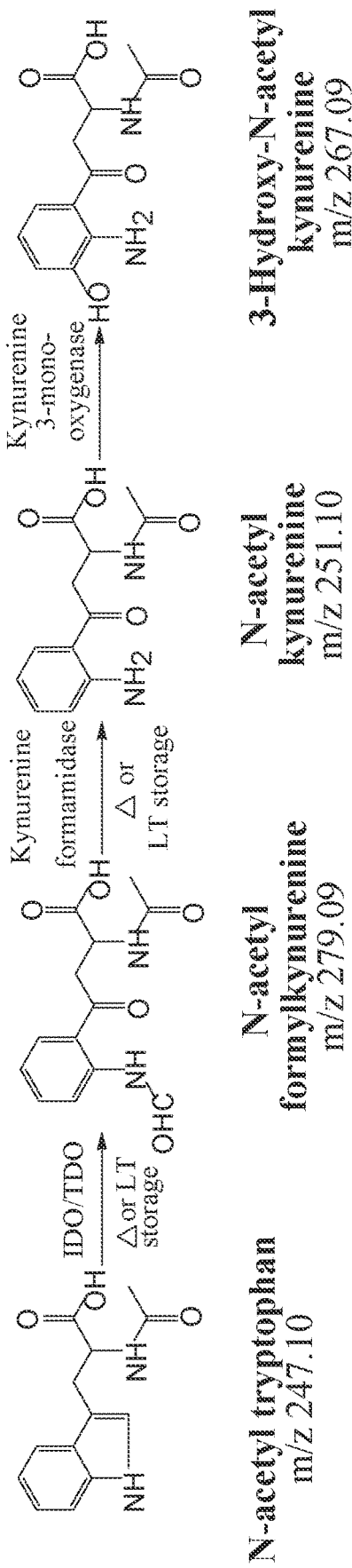
FIG. 4: Proposed non-enzymatic breakdown of NAT in LMWFSA. Under thermal forced degradation conditions (A) or long-term (LT) storage at ambient temperature of LMWFSA, the peak corresponding to the molecular weight of N-acetyl kynurenine ([M+]=251.10) significantly increases. Also, [M+]=279.09 increases with thermal forced degradation conditions in LMWFSA suggesting the increased production of the precursor (N-acetyl formylkynurenine) to N-acetyl kynurenine. Finally, the mass ([M+]=267.09) corresponding to a product (3-hydroxy-N-acetyl kynurenine) of N-acetyl kynurenine metabolism is present in LMWFSA but did not increase with heat indicating that an enzyme (kynurenine 3-mono-oxygenase) is necessary. The other enzymes involved in the metabolism of NAT are also included (IDO/TDO and kynurenine formamidase).

In addition to N-acetyl kynurenine, other significant components of LMWFSA were identified by LCMS. These components could also be related to breakdown products of NAT and include N-acetyl formylkynurenine (m/z 279.09) and 3-hydroxy-N-acetyl kynurenine (m/z 267.09) (FIG. 4). As previously mentioned, heat or long-term storage increases the production of N-acetyl kynurenine in LMWFSA. The mass (m/z 279.09) corresponding to N-acetyl formylkynurenine, the precursor to N-acetyl kynurenine, increases by 20-25% with heat indicating that formation of this degradation product of NAT can be achieved non-enzymatically. The mass (m/z 267.09) corresponding to 3-hydroxy-N-acetyl kynurenine, a product of N-acetyl kynurenine metabolism, is present in LMWFSA (FIG. 4). However, this mass does not increase with heat indicating that the formation of this degradation product is probably only achieved with an enzyme (kynurenine 3-mono-oxygenase, KMO).

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A dosage form, comprising:
   N-acetyl-kynurenine, or a pharmaceutically acceptable salt thereof;
   a second active agent; and
   a pharmaceutically-acceptable carrier.

2. The dosage form of claim 1, further comprising:
   one or more excipients; and
   one or more isotonic agents.

3. The dosage form of claim 1, wherein the amount of N-acetyl-kynurenine in the dosage form is selected from greater than about 50 µM, about 60 µM, about 70 µM, about 80 µM, about 90 µM and about 100 µM.

4. The dosage form of claim 1, wherein the amount of N-acetyl-kynurenine in the dosage form is selected from about 1 µM-about 200 µM and about 20 µM-about 100 µM.

5. The dosage form of claim 1, wherein the second active agent is selected from an analgesic, an anti-inflammatory drug and combinations thereof.

6. The dosage form of claim 1, wherein the second active agent is N-acetyl tryptophan.

7. The dosage form of claim 1, wherein the pharmaceutically-acceptable carrier is propylene glycol, water, or both propylene glycol and water.

8. The dosage form of claim 2, wherein the one or more excipients are a vegetable oil, a cellulose derivative, or both a vegetable oil and a cellulose derivative.

9. The dosage form of claim 2, wherein the isotonic agent is sodium chloride.

10. The dosage form of claim 1, which is formulated as a powder, an ointment, a paste, a cream, a gel, or a patch.

11. The dosage form of claim 1, which is formulated as a cream.

12. A method of treating an inflammatory disease, comprising administering the dosage form of claim 1 to an animal.

13. The method of claim 12, wherein the dosage form is administered transdermally.

14. The method of claim 12, wherein the dosage form is administered topically.

15. A cream, comprising:
   N-acetyl-kynurenine, or a pharmaceutically acceptable salt thereof;
   N-acetyl tryptophan;
   propylene glycol;
   water;
   vegetable oil;
   a cellulose derivative; and
   sodium chloride.

16. The cream of claim 15, wherein the amount of N-acetyl-kynurenine in the cream is selected from greater than about 50 µM, about 60 µM, about 70 µM, about 80 µM, about 90 µM and about 100 µM.

17. The cream of claim 15, wherein the amount of N-acetyl-kynurenine in the cream is selected from about 1 µM-about 200 µM and about 20 µM-about 100 µM.

18. A method of treating a T-cell-mediated disease, comprising:
   administering a cream, comprising:
      N-acetyl-kynurenine, or a pharmaceutically acceptable salt thereof;
      N-acetyl tryptophan;
      propylene glycol;
      water;
      vegetable oil;
      a cellulose derivative; and
      sodium chloride;
   to an animal.

19. The method of claim 18, wherein the cream is administered topically.

20. The method of claim 18, wherein the T-cell mediated disease is an inflammatory disease.

* * * * *